(12) United States Patent
Duan et al.

(10) Patent No.: US 7,981,410 B2
(45) Date of Patent: Jul. 19, 2011

(54) THERAPEUTIC TARGETING OF ESCORT PROTEINS

(75) Inventors: Roxanne Duan, Bethesda, MD (US); Michael Kinch, Laytonsville, MD (US); Michael Goldblatt, McLean, VA (US)

(73) Assignee: Functional Genetics, Inc., Gaithersburg, MD (US)

( * ) Notice: Subject to any disclaimer, the term of this patent is extended or adjusted under 35 U.S.C. 154(b) by 245 days.

(21) Appl. No.: 11/939,122

(22) Filed: Nov. 13, 2007

(65) Prior Publication Data
US 2008/0124341 A1     May 29, 2008

Related U.S. Application Data

(60) Provisional application No. 60/858,361, filed on Nov. 13, 2006.

(51) Int. Cl.
*A61K 48/00*     (2006.01)
*C07K 16/00*     (2006.01)

(52) U.S. Cl. .................................. 424/93.1; 530/387.1

(58) Field of Classification Search ........................ None
See application file for complete search history.

(56) References Cited

U.S. PATENT DOCUMENTS

| | | | |
|---|---|---|---|
| 5,679,523 A | 10/1997 | Li et al. | |
| 6,054,561 A | 4/2000 | Ring | |
| 6,383,493 B1 * | 5/2002 | Srivastava et al. | 424/193.1 |
| 6,608,177 B1 * | 8/2003 | Lusso et al. | 530/351 |
| 6,835,816 B2 * | 12/2004 | Cohen et al. | 530/387.1 |
| 7,335,468 B2 * | 2/2008 | Zavitz et al. | 435/5 |
| 7,427,468 B2 * | 9/2008 | Li | 435/5 |
| 2004/0223972 A1 * | 11/2004 | Li | 424/160.1 |
| 2005/0277123 A1 * | 12/2005 | Weiss et al. | 435/6 |
| 2005/0287525 A1 * | 12/2005 | Carter et al. | 435/6 |
| 2008/0187528 A1 * | 8/2008 | Li et al. | 424/131.1 |

FOREIGN PATENT DOCUMENTS

| | | | |
|---|---|---|---|
| WO | WO02/057427 A2 * | 7/2002 | |
| WO | WO02/094314 A1 * | 11/2002 | |
| WO | WO 2004/031209 A2 * | 4/2004 | |
| WO | WO2004071462 A2 * | 8/2004 | |

OTHER PUBLICATIONS

Demirov et al. PNAS, 2002, vol. 99, No. 2, pp. 955-960.*
Gottwein et al. J. Virol. Sep. 2003, vol. 77, No. 7, pp. 9474-9485.*
Bogers, vaccine 2004, vol. 22, pp. 2974-2984.*
BD Transduction Laboratories Cat. 611481, searched on Nov. 2008.*
Zhai et al. J. Biol. Chem., vol. 283, Issue 38, 26098-26106, Sep. 19, 2008.*
Schearwin-Whyatt et al. BioEssay, 2006, vol. 28, pp. 617-628.*
Harvey et al. Trend in Cell Biology, 1999, vol. 9, pp. 166-169.*
Freed V , J. Virol 2002, vol. 76, No. 10, pp. 4679-4687.*
Oldham et al. Journal of Clinical Oncology 2008, vol. 26, No. 11, pp. 1774-1777.*
Blot et al. Journal of Cell Science, 2004, vol. 117, pp. 2357-2366.*
Hui et al. Journal of Virology, 2006, vol. 80, No. 5, pp. 2006-2308.*
Limin Li, et al., "tsg101: A Novel Tumor Susceptibility Gene Isolated by Controlled Homozygous Functional Knockout of Allelic Loci in Mammalian Cells", *Cell*, vol. 85, pp. 319-329 (May 3, 1996).
Komano, et al. "The Interaction of HIV-1 with the Host Factors" Jpn. J. Infect. Dis., 2005, pp. 125-130, 58.

* cited by examiner

*Primary Examiner* — Bao Li
(74) *Attorney, Agent, or Firm* — Steven B. Kelber; Berenato & White

(57) ABSTRACT

The invention provides for inhibition of viral disease by the provision to a mammalian host of antibodies directed against an escort protein likeTsg 101. These proteins appear on the surface of a cell, and thus can be bound by circulating antibodies thereto. By binding escort proteins on the cell surface, budding of viral particles is inhibited. The virus infects the initial cells, but cannot escape that cell to infect the body en masse.

7 Claims, No Drawings

SEQUENCE LISTING

<160> NUMBER OF SEQ ID NOS: 1

<210> SEQ ID NO 1
<211> LENGTH: 7
<212> TYPE: PRT
<213> ORGANISM: Ebola

<400> SEQUENCE: 1

Pro Thr Ala Pro Pro Glu Tyr
 1               5

THERAPEUTIC TARGETING OF ESCORT PROTEINS

CROSS-REFERENCE TO RELATED APPLICATIONS

This application claims the benefit, under 35 U.S.C. §119(e), of U.S. Provisional Patent Application No. 60/858,361, filed on Nov. 13, 2006, which is hereby incorporated by reference in its entirety.

FIELD OF THE INVENTION

The present invention relates generally to methods and compositions for therapeutic treatment of viral infection, and in particular, mammalian animal hosts that are subject to viral infection, or susceptible to viral infection. The invention resides in the recognition that viral infection may be prevented, inhibited or reduced by targeting not the virus itself, but rather the escort proteins responsible for viral budding - that is, the release of viruses from an infected cell. By inhibiting the escort proteins through the administration or generation of antibodies specific for those escort proteins, viral budding can be inhibited or prevented, thus preventing the disease. The viral agents, trapped in the cell, die with the cell, and are removed.

BACKGROUND

Viruses, and viral diseases associated with them, have a common method of propagation. The virus itself infects a few cells in the body. Once in the cell, the viral nucleic acid, DNA or RNA, take over the cell's apparatus, making many copies of itself. An infected cell, or a significant number of infected cells, do not in and of themselves render a mammalian patient ill, even a human. Rather, it is the subsequent release of the virus from the surface of the infected cells that result in wide scale distribution of the virus throughout the body that leads to what regard as illness. It is the marshalling of the body's cellular and chemical defenses to combat this infestation of millions of viral copies that we recognize as the symptoms of viral infection, including fever, weakness, soreness and aches and pains, diarrhea and dehydration, etc. Viral infection, and in particular the symptoms identified can often lead to parasitic or opportunistic infection by secondary agents, including other weaker viruses, bacteria and the like.

Few remedies or treatments are available to combat viral disease. Antibiotics and the like are not only ineffective against viral disease, they may well exacerbate it, by inhibiting defense mechanisms that the body may otherwise bring to bear. In general, upon identification of a set of symptoms as reflecting a disease due to viral infection, or identification of the infectious virus itself, treatment relies on supporting the body's immune systems to deal with the invader. Palliatives including antipyretics and pain relievers, hydration and rest are key support measures. The body is on its own, and in the face of many viruses including a large number of retroviruses, it may not be adequate to face the challenge.

In some few cases, a vaccine or therapeutic focusing on the virus itself may be prepared. Since the 1950s, strategies have focused on preparing "killed" or inactivated forms of the virus, to induce circulating viruses in the host body, or on antisera (antibodies) effective in binding the viral invader. Neither strategy has been has been entirely effective. This due in large measure to the ability of viruses to mutate, and thereby escape the neutralizing effect of the active agent, which is a binding agent, typically an antibody, generated by administration of the passive form (active immunization due to administration of a innocuous or inactive pathogen that induces an immune response that is also effective against the live pathogen) or by administration of an effective titer of antibodies raised against the virus target. Viruses, by shedding or adding epitopes and changing the sequence of their nuclear proteins can in particular, where present, coat proteins, avoid previously effective viruses.

It has been discovered that viruses propagate out of initial infected cells by a process generally referred to as budding. In this process, the virus first invades the cell, and then generates multiple copies of itself within the invaded cell. The invaded cell will ultimately be removed by the bodies own processes. So long as the viral copies do not leave the cells, they cannot replicate the infective process in other cells, and thus do not generate the symptoms or conditions associated with the disease resulting from that viral infection. In the same fashion that a latent virus can reside within a few cells for long periods of time during which the patient is to all intents and appearances healthy, an initial viral infection trapped within a few cells does not pose a health risk, or even inconvenience to the mammalian animal so infected. It is when the virus copies escape from the cell, a process known as budding, that real disease begins.

Budding is effected by "hijacking" a series of proteins and protein complexes, called escort proteins, that carry the virus to the cell membrane, and help create pockets through which the virus escapes the cell. The escort proteins are residents of the cell's cytoplasm, and in normal health process, help a variety of cell synthetic products destined for intra-and-intercellular transmission cross the cell membrane. These escort proteins are not typically present outside the cell, and are ephemerally present, and uniquely accessible, as the time of viral budding. FACS analysis shows concentrations of these proteins on the cell surface at periods associated with viral budding.

An improved therapeutic system for combating viral disease is a goal sought by many. Given the incredible differentiation between viruses, and the mutational abilities of these viruses, no single strategy or agent targeted at the virus is likely to be broadly effective, even within a given virus family, let alone across those families. Even if one does not count the cost in terms of human and commercial animal deaths due to viral infection, the incredible loss of productivity and commercial product, and the billions of dollars of cost in health care and support devoted to viral care annually, make it clear that an improved strategy for treatment of viral infection is required.

SUMMARY OF THE INVENTION

The identification of a family of escort proteins that appear on the surface of a cell only in conjunction with viral budding offers a new, improved target in the therapeutic treatment of viral diseases. Accurate targeting of these escort proteins by circulating antibodies and related ligands. Binding of the escort proteins effectively inhibits the ability of the virus to bud, or leave the cell. This in turn neutralizes the infection—it is trapped in the infected cell, and as that cell dies, is removed from the body. The escort protein family that has been identified includes the following proteins: TSG101 (aka VPS23), NEDD4, VPS28, VPS28p, STP22, VPS37C, Aip1 (aka Alix), Hrs, Vps4B and ALG2. In the practice of this invention, therapeutically effective amounts—that is, amounts sufficient to inhibit viral budding from an infected cell in the body of the host—are generated or administered. They may be generated (by administering to the host an immunogenic "mimic" of the escort protein or the protein itself to induce an antibody response) or provided (passive administration) prophylactically or adventitiously, in response to possible infection—for example, by exposure to a source of the infection, in connection with chronic infection. Administration could be seasonally predicted, for example, to prevent wide scale suffering from influenza, or administered selectively to a group particularly susceptible to a given virus, such as RSV. A wide variety of administration protocols can be envisioned.

In many cases, a most effective treatment will be predicated on the administration of one multi-valent agent, or a "cocktail" of escort protein binding agents, to ensure the escape of virus particles from the infected cell is inhibited.

DETAILED DESCRIPTION

Escort proteins come to the cell surface in connection with viral budding. Thus, they are accessible to circulating agents at a uniquely valuable moment, and not otherwise. Administering to the host, or generating within the host, antibodies that bind to the escort proteins (1 or more) offers a method of inhibiting viral budding, and thus inhibiting or preventing viral disease, that is not dependent on the structure or character of the virus, and therefore not subject to loss of effectiveness due to mutations. As the structure of these escort proteins is specifically tied to the functions they perform within the cell, significant changes would not be expected over time. By the same token however, although these escort proteins are ubiquitous with the host, inhabiting virtually every cell, other than possibly some highly differentiated cells, because the proteins are not present on the surface of the cell other than for viral budding, there will not be indiscriminate binding of the antibodies to cell surfaces or structures in the body. The effect will not be diluted, nor will the "cure" be made worse than the disease, by binding of the therapeutic agent, in its purest form, an antibody, to targets not involved with viral disease.

It is well established that antibodies to these escort proteins can be prepared. Antibodies to NEDD4 are widely available. For example, antibody 2740 from Cell Signaling Technologies of Massachusetts is commercially available. Santa Cruz Biotechnology of California makes antibodies to a large number of these escort proteins available on a commercial basis, including antibodies to VPS28, ALIX, VPS28, VPS4B and ALG-2. TSG-101 is perhaps the best studied of these escort proteins. The protein product of the TSG101 gene was originally identified by the reversible neoplasia associated with its functional inactivation in murine fibroblasts (Li, L. & Cohen, S. N., 1996, Cell 85, 319-329. Since that time, a wide variety of effort has been devoted to studying this protein and its gene. See, for example, U.S. Pat. Nos. 5,679,523 and 6,835,816, both incorporated herein by reference. Santa Cruz Biotechnology (SBCT) as well as 28 others manufacture and sell antibodies to TSG101. Functional Genetic, Inc. of Maryland, the assignee of the invention disclosed and claimed herein, has developed a large number of TSG101 targeting antibodies, including a full human antibody CB-8 and a rabbit antibody 4-8A4 demonstrated as effective in inhibiting viral disease including influenza, HIV, RSV and Ebola, demonstrating the broad scope effectiveness of this invention. Functional Genetics will make available reasonable amounts of thee antibodies to third parties under conditions restricting dissemination of the antibodies to others, and the commercial use thereof, until a deposit pursuant to Budapest Treaty terms is completed.

Thus, while the above-described antibodies have not been certified as suitable for therapeutic administration to humans, the generation of antibodies to these proteins is well established, and antibodies specific therefore, and in particular, monoclonal antibodies that bind specifically to one or more escort proteins, is straight forward. Methods of modifying such antibodies, usually prepared using conventional hybridoma techniques (fusion of an antibody expressing cell such as a liver cell with an immortal myeloma cell) are similarly well known. An extensive discussion of methods of providing monoclonal antibodies (mAb) that are suitable for use for human therapy, and therefore mammalian therapy in general, from mAb prepared through conventional hybridoma lines is set forth in U.S. Pat. No. 6,054,561, incorporated herein by reference.

Importantly, an alternate strategy involves inducing an immune response in the mammalian target or host. A wide variety of inoculation techniques are known to those of skill in the art. As observed above, these escort proteins are not circulating proteins, nor are they generally presented to the mammalian immunoreactive system. They should be immunogenic in their own right. A variety of methods of conjugating these proteins with tags and flags, to induce immunogenicity is also known. These endogenous immunogens then induce an antibody immune response of sufficient circulating titre to prevent or inhibit viral disease.

As noted, in desired embodiments of the invention, the therapeutic agent reflects a combination of antibodies or similar binding ligands, or one or more multivalent (or at least bivalent) antibodies. As one example of a multivalent antibody a bi-specific reagent (e.g., antibodies or avimers) with at least two separate domains, at least one directed against Tsg101 and one directed against NEDD4, can be provided. For example, Ebola VP40 has a PTAPPEY late domain [SEQ. ID NO.: 1] where PTAP binds to TSG 101 and PPEY binds to Nedd4. These domains act independently. However, knockout (and therefore binding) of TGS 101 and NEDD4 each inhibit viral budding. An antibody which binds to each of these domains will be more effective in inhibiting or preventing viral disease than an equal amount of a monovalent agent.

The targeting entity (e.g., antibody) could be armed with any of a variety of different modifications to increase therapeutic efficacy, including but not limited to: a covalently-linked toxin (chemical or biological) that functions intracellularly, an antibody-directed enzyme prodrug therapy (or ADEPT-like) technologies that function at the cell surface, or a fusion of the antibody with a toxin or efficacy-enabling or enhancing partner. These could include bi- or multi-specific antibodies (e.g., targeting CD3 or CD16 to trigger T or NK cell killing of targets). Likewise, mono- or multi-specific targeting could be achieved with antibody-based entities (containing a Fab or Fc domain), including but not limited to mini-bodies, BiTEs or Fc fusions). Mono- or multi-specific targeting could be achieved by non-antibody entities, including but not limited to avimers and other protein scaffolds, which are capable of binding escort proteins such a TSG1011 alone or in combination with a toxin or an entity (e.g., ligand) promoting other effector mechanisms. Whether the antibody is provided passively, by injection, or actively, by inoculation with an immunogen, an effective amount will be sufficient to support circulating tiers of the antibody provided in a range effective to inhibit viral budding throughout the body, and thus inhibit viral disease. It is not possible to identify a specific antibody titer that is effective. The effective titer will vary with species, individual, viral type and antibody. Methods known to those of skill in the art allow the practitioner to titrate to an acceptable value. As an inoculation, effective amounts may range from about 10 ng/kg to up to 100 mg/kg of mammal body weight or more per day, preferably about 1 µg/kg/day to 10 mg/kg/day. As a passive vaccine, or when trying to identify a circulating titer that is desirable, values ranging from 1 µg/ml up to about 1000 mg/ml are targets.

The strategies listed above could be applied to multiple and different pathogens, including viral diseases linked with escort protein, including but not limited to: HIV-I, HIV-II, HTLV-T and other retroviruses; Ebola, Marburg and other hemorrhagic fever viruses; all strains and clades of influenza (H5N1, H3N2, H1N1, etc); respiratory syncytial virus (RSV), Human metapneumovirus (HMPV), adenovirus, rhinovirus, and other respiratory viruses, (particularly those contributing to morbidity and mortality of pre-mature or immuno-compromised infants); and all other viruses linked with chronic infection or inflammation, including HBV, HCV, EBV, and herpesvirus.

These applications could include prophylaxis or therapy of new or existing disease. One example is prophylactic application in susceptible populations include RSV infection of infants or HIV-infected persons as well as a hemorrhagic fever infection in all patients. This could occur on a one-time (e.g., bioterrorism), intermittent (e.g., prophylaxis of sexually transmitted disease at or near time of exposure), or on a seasonal (e.g., influenza or RSV) basis. Therapeutic applications could include patients with active or acute infection (at the time of clinical presentation), with chronic infection (e.g., HBV, HCV, HIV), or patients that have been previously exposed to a particular virus and are at risk of reemergence (e.g., HIV or other retroviruses, lentiviruses, and/or herpesviruses as in the case of shingles or recurrent herpes infection.

Another embodiment for escort protein targeting would arise in situations where more than one virus is associated with a disease. For example, there is evidence that multiple and different hepatotropic viruses (HBV, HCV, HDV and/or HIV) are often transmitted or infectious in the same individual and the resulting hepatitis super-infection is generally associated with more debilitating chronic hepatitis than indications associated with a single infection. Likewise, infection with HIV-1 may contribute to the development of HTLV-2 malignant lymphoproliferative processes. Thus, intervention against one or more of the escort proteins, which are expected to be applicable to both contributing agents, could provide more effective therapy than targeting of individual viruses.

Another embodiment of this invention could arise in situations where viruses cooperate with other pathogens to mediate disease. Examples include respiratory or pneumonic diseases where viral infection (by influenza virus, parainfluenza viruses, respiratory syncytial virus (RSV), adenoviruses, measles virus, rhinovjruses, and coronaviruses) triggers concomitant or subsequent infection by bacterial species (e.g., resident *Streptococcus pneumoniae, Streptococcus pyogenes, Haemophi lus infiuenzae, Staphylococcus aureus, Neisseria meningitidis, Mycobacteijum tuberculosis, Bordetella pertussis,* or *Pseudomonas aeruginosa*). Similarly, otitis media has been linked with a cooperative infection by a virus (RSV, influenza (A or B) virus, or adenovirus) and a bacterium (*Streptococcus pneumoniae* or *Haemophilus influenzae*). Similarly, mixed viral-bacterial infections are common in human gastroenteritis. Finally, infections with herpesviruses (cytomegalovirus, HSV, HHV6, HHV7, HHV8), Epstein-Barr virus type 1 (EBV-1), and HCMV/EBV-I dual infection) have recently been linked with infection and damage by periodontopathic bacteria, including *Aetinobacillus actinomycetemcomitans, Porphyromonas gingivalis, Dialister pneumosintes, Prevotella intermedia, Prevotella nigrescens,* and *Treponema denticola.*

Antibody targeting of escort proteins could also have application to prevent or ameliorate the morbidity or mortality of diseases directly or indirectly associated with viral infection. Examples include asthma or wheezing associated with, or triggered by, respiratory viral infection (e.g., RSV, influenza, rhinovirus, HMPV or adenovirus-associated asthma in children).

Likewise, targeting of escort proteins could have utility in minimizing the damage (or enhancing the subsequent repair) of other virally-linked diseases, including inflammatory diseases associated with infection (rheumatoid arthritis, inflammatory bowel disease, hepatitis) and/or fibrotic diseases that are associated with inappropriate repair following initial damage. As a specific example, HHV-6, MSRV, measles virus, and EBV have each been linked with the development and recurrence of multiple sclerosis (MS). It is therefore possible that therapeutic targeting of Tsg101 could be useful to prevent the incidence, severity or frequency of MS or MS-mediated morbidity or mortality.

Indeed, the escort protein binding strategy of this invention is applicable to inhibition of viral disease independent of the nature or character of the virus. In this respect, Applicants note with particularity that what is described is NOT a method of inhibiting viral infection, although it may ultimately be of value in frustrating viral infection. Instead, this is a method of inhibiting or preventing viral disease. The symptoms and conditions associated with viral disease are prevented independent of the nature and character of the virus, as the target of the therapeutic agent is not the virus, but the escort protein it is dependent on to escape the infected cell. Thus, this strategy should be effective in treating a mammalian individual, including not only humans, apes and veterinary subjects such as dogs and cats, but commercial animals such as pigs and cows. All members of the seven recognized classes of viruses, as discussed below, should be susceptible to this method of treatment.

| Virus Family | Virus Genus | Virion-naked/enveloped | Capsid Symmetry | Type of nucleic acid |
|---|---|---|---|---|
| 1. *Adenoviridae* | Adenovirus | Naked | Icosahedral | ds |
| 2. *Papovaviridae* | Papillomavirus | Naked | Icosahedral | ds circular |
| 3. *Parvoviridae* | B 19 virus | Naked | Icosahedral | ss |
| 4. *Herpesviridae* | Herpes Simplex Virus, Varicella zoster virus, Cytomegalovirus, Epstein Barr virus | Enveloped | Icosahedral | ds |
| 5. *Poxviridae* | Small pox virus, Vaccinia virus | Complex coats | Complex | ds |
| 6. *Hepadnaviridae* | Hepatitis B virus | Enveloped | Icosahedral | ds circular |
| 7. *Polyomuviridae* | Polyoma virus (progressive multifocal leucoencephalopathy) | | | ds |

A potential new method of combating the morbidity and mortality associated with viral infection is provided. By inhibiting viral budding through binding of escort proteins when located on the surface (exposed) of cells—which specifically in connection with viral budding—escape of the virus from an infected cell, and thus, disease manifestation, is prevented.

What is claimed is:

1. A method of inhibiting viral disease caused by an enveloped virus selected from the group consisting of influenza, parainflueza or respiratory syncytial virus (RSV), which comprises providing to said mammal an effective amount of at least one antibody that binds Nedd4 on a surface of cells of said mammal infected by said enveloped virus, and thereby inhibits said viral disease.

2. The method of claim 1, wherein said antibody is provided to said mammal by injecting said mammal with an amount of said antibody sufficient to provide an effective circulating titer of said antibody.

3. The method of claim 1, wherein said antibody is provided to said mammal by inoculating said mammal with an agent which induces an antibody generating immune response in said mammal, wherein antibodies generated by said response bind to Nedd4m, wherein said agent is Nedd.

4. The method of claim 1, wherein said antibody is provided to said mammal in association with an exposure of said mammal to a source of said virus which induces said viral disease in said mammal.

5. The method of claim 1, wherein said mammal is a human.

6. The method of claim 1, wherein said mammal is a commercial animal selected from the group consisting of pigs, sheep, cows, horses and goats.

7. The method of claim 1, wherein said antibody is a monoclonal antibody modified to be acceptable for therapeutic administration to humans.

* * * * *